United States Patent
Ripplinger et al.

(10) Patent No.: US 9,656,977 B2
(45) Date of Patent: May 23, 2017

(54) POLYAMIDE HARDENERS FOR EPDXY RESINS

(71) Applicant: Dow Global Technologies LLC, Midland, MI (US)

(72) Inventors: Eric B. Ripplinger, Lake Jackson, TX (US); Rajesh H. Turakhia, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 34 days.

(21) Appl. No.: 14/432,870

(22) PCT Filed: Oct. 22, 2013

(86) PCT No.: PCT/US2013/066178
§ 371 (c)(1),
(2) Date: Apr. 1, 2015

(87) PCT Pub. No.: WO2014/066386
PCT Pub. Date: May 1, 2014

(65) Prior Publication Data
US 2015/0252012 A1    Sep. 10, 2015

Related U.S. Application Data

(60) Provisional application No. 61/717,698, filed on Oct. 24, 2012.

(51) Int. Cl.
| | |
|---|---|
| *C07D 233/24* | (2006.01) |
| *C07D 295/13* | (2006.01) |
| *C08G 59/14* | (2006.01) |
| *C08G 59/50* | (2006.01) |
| *C08G 69/34* | (2006.01) |
| *C08G 73/02* | (2006.01) |
| *C08G 73/06* | (2006.01) |
| *C09D 163/00* | (2006.01) |
| *C09J 163/00* | (2006.01) |
| *C08L 63/00* | (2006.01) |
| *C08L 77/08* | (2006.01) |
| *C08L 79/02* | (2006.01) |
| *C08L 79/04* | (2006.01) |
| *C08G 59/44* | (2006.01) |

(52) U.S. Cl.
CPC ......... *C07D 295/13* (2013.01); *C07D 233/24* (2013.01); *C08G 59/1477* (2013.01); *C08G 59/44* (2013.01); *C08G 59/5073* (2013.01); *C08G 69/34* (2013.01); *C08G 73/028* (2013.01); *C08G 73/0273* (2013.01); *C08G 73/0633* (2013.01); *C08L 63/00* (2013.01); *C09D 163/00* (2013.01); *C09J 163/00* (2013.01); *C08L 77/08* (2013.01); *C08L 79/02* (2013.01); *C08L 79/04* (2013.01)

(58) Field of Classification Search
CPC .. C08G 59/44; C08G 73/0273; C08G 73/028; C08G 73/0633; C08G 69/34; C08G 59/5073; C07D 295/13; C07D 233/24; C08L 63/00–63/10; C08L 77/08; C08L 79/02; C08L 79/04; C09D 163/00–163/10; C09J 163/00–163/10
See application file for complete search history.

(56) References Cited

U.S. PATENT DOCUMENTS

| | | | |
|---|---|---|---|
| 4,082,709 A | 4/1978 | Dyckman et al. | |
| 4,990,672 A * | 2/1991 | Johnson | C07C 209/48 544/357 |
| 5,256,786 A * | 10/1993 | Bowman | C07D 295/13 544/357 |
| 5,385,986 A * | 1/1995 | Frihart | C08L 77/00 525/420.5 |
| 2014/0349049 A1* | 11/2014 | Chang | C08G 59/5073 428/35.8 |

FOREIGN PATENT DOCUMENTS

| | | |
|---|---|---|
| GB | 726570 | 3/1955 |
| GB | 873224 | 7/1961 |
| WO | 0035986 | 6/2000 |

OTHER PUBLICATIONS

Bajpai et al., "Synthesis of Plasticizing Polyesters of Dimer Acid and Propane-Diol," J. Appl. Polym. Sci. 50, 693-697 (1993).*
Ash et al., Handbook of Plastic and Rubber Additives, 2nd ed., vol. 1-2, p. 1613 (2013).*
Scifinder properties of 60-33-3 (2015).*
Bazzicalupi, C, et al., Syntehtic Route to Produce Giant-Sixe Azamacrocycles, Journal of Organic Chemistry, 1994, pp. 7508-7510, vol. 59.
Chen, et al., International Journal of Adhesion and Adhesives, 2002, pp. 75-79, vol. 22.
International Preliminary Report on Patentability for PCT/US2013/066178, 2015, pp. 1-6.
Search Report and Written Opinion of the International Searching Authority for PCT/US2013/066178, 2014, pp. 1-10.

* cited by examiner

*Primary Examiner* — Kregg Brooks
(74) *Attorney, Agent, or Firm* — Andrew Merriam

(57) ABSTRACT

A polyamide composition comprising a reaction product of: a) an excess of a polyfunctional amine; b) a dimer fatty acid; and c) a monomer fatty acid is disclosed. The polyamide composition can be used as a hardener in epoxy resin formulations.

18 Claims, No Drawings

POLYAMIDE HARDENERS FOR EPDXY RESINS

BACKGROUND OF THE INVENTION

Field of the Invention

The present invention is related to epoxy resins. More particularly, the present invention is related to hardeners for epoxy resins.

Background of the Invention

This invention relates to new polyamide compositions and their use as hardeners for epoxy resins. The new polyamides are the reaction products of bis(2-(piperazin-1-yl)ethyl)amine (BPEA) with dimer and monomer fatty acids. The BPEA polyamides give faster cure rates with epoxy resins and the cured composition exhibits higher flexibility compared to standard polyamides made from polyalkyleneamines (e.g. triethylenetetramine (TETA)). In addition, the BPEA polyamide gives a lower onset cure temperature with epoxy resins than TETA polyamides. This allows the use of BPEA polyamides in lower temperature applications than is possible with standard polyamides. In coatings applications, the BPEA polyamides give better film appearance and do not require an induction time.

Another aspect of this invention relates to polyamide composition in which the polyamide is the reaction of excess amine mixture of BPEA and other polyamine with dimer and monomer fatty acids.

Another aspect of this invention is the use of BPEA polyamides as a modifier in epoxy thermosets. The BPEA polyamide can be blended with any other amine hardeners, e.g. TETA based polyamides, aliphatic amines (hexamethylenediamine), polyalkyleneamines (e.g. TETA), cycloaliphatic amines (e.g. isophoronediamine), aromatic amines (e.g. methylenedianiline), hererocyclicamines (e.g. aminoethylpiperazine), and aryl-aliphatic amines (e.g. m-xylenediamine), and the resulting blend can be used to cure epoxy resins. In this way, the reactivity of the formulation and final properties of the cured epoxy thermoset can be varied to meet the formulator's needs.

SUMMARY OF THE INVENTION

One broad aspect of the present invention is a polyamide composition comprising, consisting of, or consisting essentially of a reaction product of: a) an excess of a polyfunctional amine; with at least one of b) a dimer fatty acid and c) a monomer fatty acid.

DETAILED DESCRIPTION OF THE INVENTION

Polyfunctional Amine

The preferred polyfunctional amine compound comprises at least two cyclic rings that each have at least two amine groups separated from one another by a binary carbon spacing (C2 spacing) in each cyclic ring In a preferred embodiment for example, the generic Formula I and II, set forth below, represent examples of the cyclic polyfunctional amine compounds useful in the present invention.

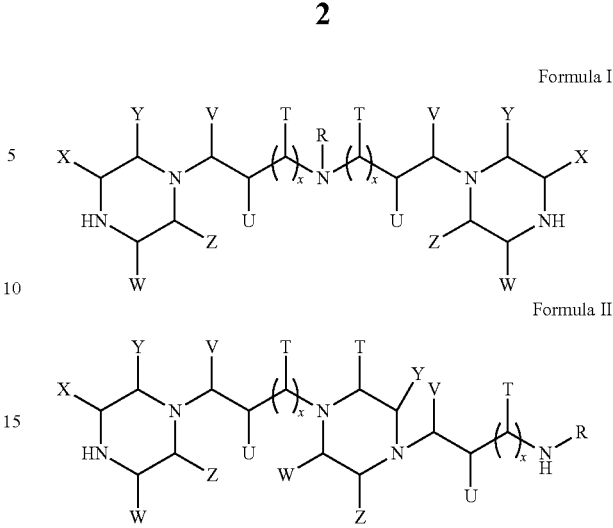

wherein each R, T, U, V, W, X, Y, and Z group, in Formula I and II above, is the same or different and is selected from hydrogen, or a hydrocarbyl group; and the value of x is 0 to 10, with the proviso that if x is greater than 1, each T may be the same or different.

Hydrocarbyl groups that may be used in the practice of the invention may be substituted or unsubstituted, linear, branched, or cyclic hydrocarbyl such as alkyl, aryl, aralkyl, or the like; a monovalent moiety including one or more heteroatoms; polyether chains comprising one or more oxyalkylene repeating units such as —$R^1$O—, wherein $R^1$ is often alkylene of 2 to 5 carbon atoms; other oligomeric or polymer chains of at least 2 repeating units. In an embodiment, R, T, U, V, W, X, Y, and Z are H or straight, branched, or cyclic hydrocarbyl such as alkyl of 1 to 10 carbon atoms, preferably 1 to 3 carbon atoms. In another embodiment, R, T, U, V, W, X, Y, and Z are H.

The values of x in the practice of the invention are typically in the range of from 1 to 10, preferably in the range of from 2 to 5, and more preferably in the range of from 2 to 3.

Examples of cyclic polyamines consistent with Formula I that are useful in the present invention include bis(2-(piperazin-1-yl)ethyl)amine (BPEA), (3-(piperazin-1-yl)propyl)amine, bis(4-(piperazin-1-yl)butyl)amine, bis(5-(piperazin-1-yl)pentyl)amine, bis(6-(piperazin-1-yl)hexyl)amine, bis(1-(piperazin-1-yl)propan-2-yl)amine, bis(2-(piperazin-1-yl)propyl)amine, and mixtures thereof.

Examples of cyclic polyamines consistent with Formula II that are useful in the present invention include 2-(4-(2-(piperazin-1-yl)ethyl)piperazin-1-yl)ethanamine, 3-(4-(3-(piperazin-1-yl)propyl)piperazin-1-yl)propan-1-amine, 4-(4-(4-(piperazin-1-yl)butyl)piperazin-1-yl)butan-1-amine, 5-(4-(5-(piperazin-1-yl)pentyl)piperazin-1-yl)pentan-1-amine, 6-(4-(6-(piperazin-1-yl)hexyl)piperazin-1-yl)hexan-1-amine, 1-(4-(1-(piperazin-1-yl)propan-2-yl)piperazin-1-yl)propan-2-amine, 2-(4-(2-(piperazin-1-yl)propyl)piperazin-1-yl)propan-1-amine, and mixtures thereof.

One preferred embodiment of the cyclic polyamine compound useful in preparing the adduct of the present invention includes for example bis(2-(piperazin-1-yl)ethyl)amine (BPEA); high molecular weight BPEA oligomers; and mixtures thereof.

In an embodiment, the polyfunctional amine is present in excess. Only the secondary amine groups of BPEA can react with a carboxylic acid to make polyamides. Since the hardeners are amine-functional polyamides, an excess of secondary amine groups over carboxylic acid groups is used. In one embodiment, the secondary amine to carboxylic acid equivalent ratio is in the range of 1 to 12, in another embodiment the ratio is in the range of from 2.5 to 6.0.

The weight percentage of BPEA in the polyamide will typically be from 30 to 80 wt %, based on the total weight of reactants charged. Some of the BPEA may be substituted with a standard polyalkyleneamine, e.g. TETA, to give a mixed polyamide. For a mixed polyamide, the combined primary and secondary amine to carboxylic acid equivalent ratio should be in the range of 1 to 12, and in the range of 2.5 to 6.0 in another embodiment.

Dimer Fatty Acid

'Dimer fatty acids,' for the purposes of this invention, are defined to mean the same as the 'polymeric fat acids,' defined in U.S. Pat. No. 3,002,941. Commercially available dimer fatty acids are made by polymerization of drying or semi-drying oils or their free acids, particularly sources rich in linoleic acid. The dimer fatty acids may contain a high purity form of the dimer fatty acid, or a mixture of acids with a majority of dimer fatty acid, a smaller portion of trimer and higher acids, and some residual monomer fatty acid. Examples of commercially available dimer fatty acid acids useful in the present invention include, but are not limited to Unidyme 14 and Unidyme 22, produced by Arizona Chemical Company; Pripol 1013 and Pripol 1017 produced by Croda.

Monomer Fatty Acid

Monomer fatty acids are defined by the formula RCOOH where R represents an aliphatic carbon chain of 10 to 21 carbon atoms, either saturated or unsaturated, preferably with a high proportion of unsaturated acids. Examples of monomer fatty acids include but are not limited to fatty acids are derived from tall oil, soybean oil, tallow, cottonseed oil, and other animal and vegetable sources. C18 acids, such as oleic acid and linoleic acid, are the most common.

The dimer fatty acid and the monomer fatty acid can be used alone or in combination to react with the polyfunctional amine to form a polyamide composition. The concentration ratio of the dimer fatty acid and the monomer fatty acid above can be adjusted in any proportions so long as the combined primary and secondary amine to carboxylic acid equivalent ratio is in the range of 1 to 12, or preferably 2.5 to 6.0 as described above. For instance, in one embodiment, a dimer fatty acid to monomer fatty acid weight ratio of about 6:1 may be used. In another embodiment, a dimer fatty acid to monomer fatty acid weight ratio of about 0.15:1 can be used.

Generally, the dimer fatty acid is present in an amount in the range of from 0 weight percent to 100 weight percent, based on the combined total weight of the monomer fatty acid and the dimer fatty acid. The dimer fatty acid is present in an amount in the range of from 70 weight percent to 95 weight percent in another embodiment, and is present in an amount in the range of from 5 weight percent to 25 weight percent in yet another embodiment, based on the combined total weight of the monomer fatty acid and the dimer fatty acid.

Other Reactants

In addition to a dimer and/or monomer fatty acid, other polycarboxylic acids can be used to react with the polyfunctional amine to form a polyamide composition. Examples of polycarboxylic acids include, but are not limited to polycarboxylic acids derived from addition of carbon monoxide to unsaturated higher fatty acids, dicarboxylic acids from sources other than unsaturated higher fatty acids, and mixtures thereof.

Polycarboxylic acids derived from addition of carbon monoxide to unsaturated higher fatty acids are defined in U.S. Pat. No. 3,062,773. Examples include the polycarboxylic acid made from addition of carbon monoxide to tall oil fatty acids.

Dicarboxylic acids from sources other than unsaturated higher fatty acids can include any dicarboxylic acid not derived from unsaturated higher fatty acids which have the general formula HOOC—R—COOH, where R can be an alkyl, alkenyl, alkynal, or aryl group. Examples include sebacid acid (HOOC(CH$_2$)$_8$COOH) and terephathalic acid (benzene-1,4-dicarboxylic acid).

In an embodiment, an additional amine compound can be added to the polyfunctional amine component. The additional amine can be any polyalkyleneamine such as but not limited to diethylenetriamine (DETA), triethylenetetramine (TETA), tetraethylenepentamine (TEPA), and combinations thereof.

In an embodiment of the present invention, there is also disclosed a method for preparing a polyamide composition comprising contacting a) the polyfunctional amine described above; with at least one of b) a dimer fatty acid; and c) a monomer fatty acid in a reaction zone under reaction conditions.

Generally, the reaction conditions comprise a reaction temperature of 70° C. to 300° C. under a nitrogen atmosphere, while stirring and simultaneously distilling off any water that is formed. In an embodiment, the dimer fatty acid and/or monomer fatty acid are added to the reactor, the BPEA and optionally other amines are then added gradually such that the reaction temperature does not exceed about 120° C. The mixture is digested for 45 minutes, then gradually heated at about 1° C. per minute to a temperature of 180° C., then held for 15 to 30 minutes. The mixture is then heated to 230 to 250° C. at approximately 1° C. per minute, then held for 15 minutes and sampled. If necessary, heating may be continued until the reaction is completed. Operation at reduced pressure (e.g. 150 mm Hg absolute pressure) may be used to increase the rate of water removal at a given temperature to drive the reaction to completion. This is especially useful when heating capacity is limited.

The polyamide compositions of the present invention can have a variety of structures. The polyamide hardener composition is typically an oligomeric composition comprising one or more polyamide compositions, including but not limited to polyamide compositions having structures shown below.

The polyamide shown as Formula III, below, is obtained by the reaction of a dimer fatty acid with two molecules of BPEA.

Formula III

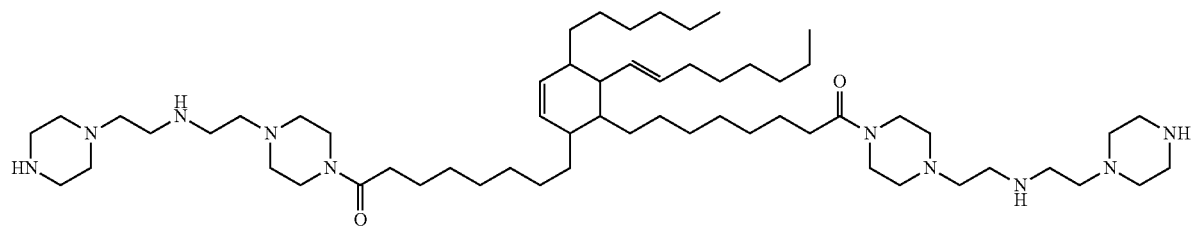

The polyamide composition shown as Formula IV, below, is a low viscosity polyamide obtained by the reaction of a monomer fatty acid with BPEA.

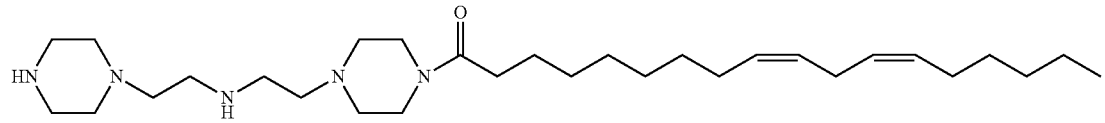

Formula IV

A polyamide composition that can be obtained by the reaction of dimer fatty acid with two molecules of BPEA, followed by reaction of one of the remaining NH groups of one BPEA moiety with a monomer fatty acid is shown as Formula V, below.

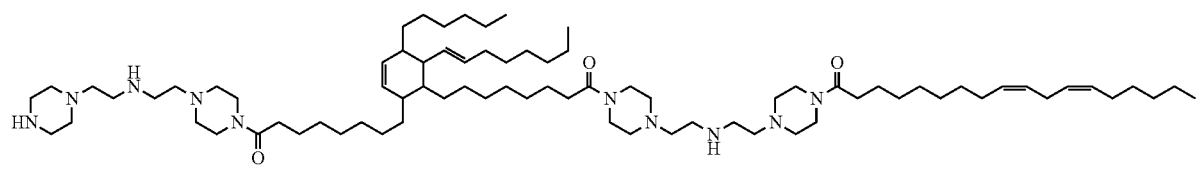

Formula V

Numerous other types of BPEA-containing polyamide structures are possible by incorporation of other amines or dicarboxylic acids during the reaction. One example of a mixed polyamide produced by a reaction of a dimer fatty acid with BPEA and TETA is shown as Formula VI, below.

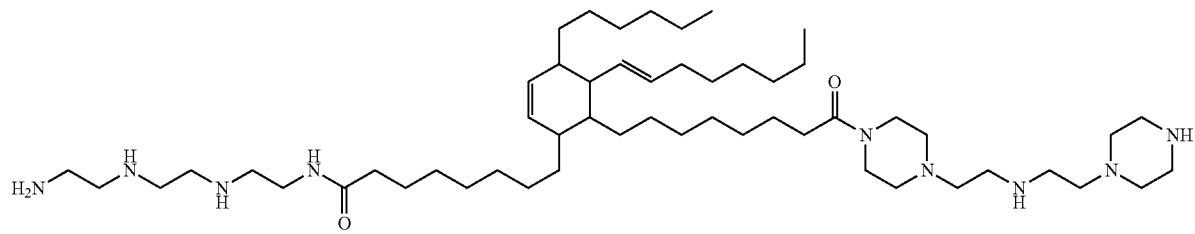

Formula VI

The amide group formed from reaction of TETA with the dimer fatty acid, see Formula VI, can undergo further condensation reaction by heating to form an imidazoline, shown in Formula VII, below. The conversion of amide to imidazoline is known to reduce the viscosity of polyamide hardeners which is desirable in some applications.

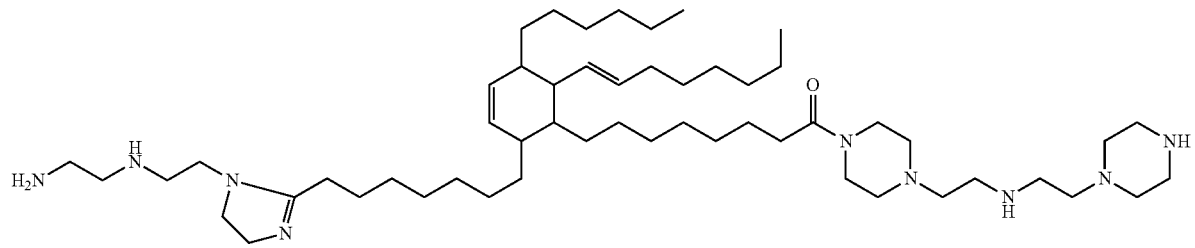

Formula VII

Another broad aspect of the present invention is a curable composition comprising, consisting of, or consisting essentially of: a) an epoxy resin; and b) a hardener comprising the polyamide composition described above.

Epoxy Resin

Any suitable aromatic, aliphatic, or cycloaliphatic epoxy resin can be used in the curable composition. The epoxy resin can be a liquid, solid, or a solution of the resin in solvent. Examples of epoxy resins include, but are not limited to bisphenol-A epoxy resins such as D.E.R.™ 331, and D.E.R.™ 383, bisphenol-A epoxy resin blends with reactive diluents, such as D.E.R.™ 323 and D.E.R.™ 324, bisphenol-F epoxy resins such as D.E.R.™ 354, bisphenol-A/F epoxy resin blends such as D.E.R.™ 353, aliphatic glycidyl ethers such as D.E.R.™ 736; solid bisphenol-A epoxy resins such as D.E.R.™ 661 and D.E.R.™ 664 UE; solution of bisphenol-A solid epoxy resins such as D.E.R.™ 671-X75; epoxy novolac resins such as D.E.N.™ 438; and brominated epoxy resins such as D.E.R.™ 542. The epoxy resin can also be a epoxy resin blend comprising (i) an epoxy resin such as D.E.R. 383, or D.E.R. 331, or D.E.R. 354, and (ii) mono-, di-, tri-, and polyglycidylethers of aliphatic epoxy resins, monoglycidylethers of aromatic epoxy resins, and iii) other reactive and non-reactive diluents. Examples of these are D.E.R. 736, D.E.R. 732, cresyl glycidyl ether, diglycidylether of aniline, Alkyl $C_{12}$-$C_{14}$ mono glycidyl ether 1,4-butanedioldiglycidylether, 1,6-hexane dioldiglycidyl ether, 2-ethylhexylglycidyl ether, neopentlyglycidylether, trimethylpropanetriglycidyl ether, and hydrocarbon resins. Mixtures of two or more aromatic epoxy resins can also be used.

Epoxy resins are formulated with the polyamide hardeners at an epoxide to amine hydrogen (NH) equivalent ratio of 0.7 to 1.3, more preferably 0.9 to 1.1, and most preferably 0.95 to 1.05. Only active NH groups are counted in the amine hydrogen equivalent calculation. In polyamide hardeners the NH group of the amide moiety (e.g. —CONH— is not active and thus is not counted in the NH equivalents.

Optional Components

Hardener

In an embodiment, a hardener other than the polyamide composition described above can be used in the curable composition. Any suitable epoxy hardener can be used. Examples of epoxy hardeners that can be used include, but are not limited to aliphatic amines, modified aliphatic amines, cycloaliphatic amines, modified cycloaliphatic amines, amidoamines, polyamide, tertiary amines, aromatic amines, and the like. Suitable hardeners include Bis(4-aminocyclohexyl)methane (AMICURE® PACM), diethylenetriamine (DETA), triethylenetetramine (TETA), aminoethylpiperazine (AEP), isophorone diamine (IPDA), 1,2-diaminocyclohexane (DACH), 4,4'-diaminodiphenylmethane (MDA), 4,4'-diaminodiphenylsulfone (DDS), m-phenylenediamine (MPD), diethyltoluenediamine (DETDA), meta-xylene diamine (MXDA), bis(aminomethyl cyclohexane), dicyandiamide, and the like, and mixtures thereof.

Catalyst

Optionally, catalysts may be added to the curable compositions described above. Catalysts may include but are not limited to salicylic acid, bisphenol A, DMP-30, and alcohol and phenol derivatives.

Other optional components can include solvents, fillers, pigments and plasticizers commonly known in the art for applications involving epoxy resins and amine hardeners. Examples of fillers are silica or talc. Other additives such as defoaming agents or surface tension modifiers can be added.

Process for Producing the Composition

In an embodiment, the curable composition can be prepared by admixing a) an epoxy resin and b) the polyamide curing agent. In an embodiment, any of the optional components described above can be added to the admixture. The admixing can be done in any order, and in any combination or sub-combination. The curable composition can be degassed by centrifugation or by applying vacuum as needed.

Process for Curing the Composition

In an embodiment, the composition is cured at a temperature in the range of from 0° C. to 200° C. In another embodiment, the composition is cured at ambient temperature. Curing at ambient temperature requires a longer time to achieve ultimate properties that curing at higher temperatures. The BPEA polyamides can give faster cure rates with epoxy resins compared to standard polyamides made from polyalkyleneamines (e.g. triethylenetetramine (TETA)). In addition, the BPEA polyamide can give a lower onset cure temperature with epoxy resins than TETA polyamides. This allows the use of BPEA polyamides in lower temperature applications than is possible with standard polyamides.

Induction time in thermoset curing applications is the period of time in which the mixed composition of epoxy resin and hardener is allowed to stand before application. Polyamides often require long induction times, sometimes as long as 24 hours, before use. The new BPEA polyamide of this invention does not require a long induction time. The compositions in the examples provided herein had no induction time or induction times of less than 30 minutes.

End Use Applications

The curable composition of the present invention can be used in a variety of applications including, but not limited to coatings, composites, adhesives, and electrical laminates.

EXAMPLES

UNIDYME 14—dimer fatty acid available from Arizona Chemical

UNIDYME 22—dimer fatty acid available from Arizona Chemical

SYLFAT FA2—monomer fatty acid available from Arizona Chemical

D.E.H.™ 24—triethylenetetramine (TETA) hardener available from the Dow Chemical Company D.E.R.™ 324—aliphatic glycidyl ether, reactive diluent modified liquid epoxy resin, available from the Dow Chemical Company D.E.R.™ 331—bisphenol A liquid epoxy resin, available from the Dow Chemical Company D.E.R.™ 671-X75—available from the Dow Chemical Company BPEA—research sample with 93.7% purity by gas chromatography, having an amine value of 1080 mg KOH/gram.

Analytical Methods for Polyamide Characterization

Amine Value Titration

Amine value was determined by potentiometric titration of samples in glacial acetic acid with 0.1N perchloric acid in glacial acetic acid. The method is based on ASTM D6979. In the case of the BPEA polyamides, the same method was used except 0.1 HBr in glacial acetic acid was used as the titrant.

Viscosity

Viscosity measurements at 25° C. were made with a Brookfield Model RVDV-II+ Cone and Plate Viscometer. The instrument was equipped with a CPE-52 cone capable of measurements between 49 cP to 983,000 cP.

Gardner Color

The color determination was performed according ASTM D5386 (standard test method for color of liquids using tristimulus colorimetry) using a Hunterlab COLORQUEST XE colourimeter. Approximately 50 g of sample was transferred into a 20-mm path length cuvette and the tristimulus values (CIE XYZ scale) of the light transmitted by the sample, as a percent of light transmitted by distilled water, were determined using illuminant C and 2° observer.

Imidazoline Content

Fourier Transform Infrared Spectroscopy (FTIR) was used to measure the imidazoline content. A Nicolet Nexus 670 FTIR spectrometer was used with Nicolet SMART DuraSampl advanced total reflectance module (Sensor Technologies Part #071-1520). The IR absorption bands of main interest are the amide (C=O, 1650 cm$^{-1}$) and the imidazoline (C=N, 1610 cm$^{-1}$). The mole percent imidazoline was calculated by: (peak height of imidazoline, C=N)×100%/ (peak height of imidazoline, C=N+peak height of amide, C=O).

Unreacted TETA and BPEA

Unreacted TETA and BPEA in the polyamides was determined by gas chromatography (GC). Samples were diluted 3:1 in methanol prior to injection. The instrument used was an Agilent HP 6890 equipped with a DB-1701 column (30 m×0.32 mm), auto injector, and FID detector. Weight percent results were reported using an external calibration method. An external calibration for aminoethylpiperazine (AEP) was used for BPEA analysis since the molecules are expected to have similar FID response factors.

Methods for Hardener Evaluations in Epoxy Thermosets

Mechanical Testing on Cured Plaques

Formulations for plaques were prepared using D.E.R.™ 324 and the hardener at a 1 to 1 epoxy to amine hydrogen (NH) equivalent ratio. Formulations (190 grams) were mixed using a Flack Tek mixer for 0.5 minute at 800 rpm followed by 2 minutes at 1600 rpm. The mixture was centrifuged for 5 minutes at 2500 rpm and then poured into molds which had been pre-warmed to 40° C. The plaques were cured for 14 hours at 60° C. Tensile strength and modulus were measured at 25° C. using an INSTRON 4505 according to ASTM D638, type 1. Flexural strength was measured at 25° C. on an INSTRON 4505 by ASTM D790. Dynamic mechanical thermal analysis (DMTA) was conducted using a TA Instruments ARES Rheometer under a torsional mode from 25° C. to 180° C. at 5° C. per step. The test frequency was 1 Hz with a strain amplitude of 0.05%. The temperature at which the tan δ peak was located was recorded as the glass transition temperature.

Gel Time

Gel time was determined by ASTM D 2471 on a Gardner Gel Timer. The formulation (100 grams) was mixed one minute with a tongue depressor, and then placed on the gel time unit.

Glass Transition Temperature (Tg)

Glass transition temperatures were determined by differential scanning calorimetry (DSC). The instrument used was a TA Instruments Model Q2000-1160 DSC. The cured samples (10 mg) were scanned twice from 0 to 200° C. at a ramp rate of 10° C./min. The Tg was determined by the half extrapolated tangents method from the heat flow versus temperature plot.

DSC Reactivity Study

Formulations (10 grams) were mixed for 1 minute at 2400 rpm using a Flack Tek mixer, and then a sample (10 mg) was loaded into a sealed hermetic pan and analyzed by differential scanning calorimetry (DSC). The sample was scanned 0 to 200° C. at 2° C. per minute scan rate. The onset temperature and the heat release for the cure exotherm were determined. After the first scan, the sample was cooled to 25° C. and scanned from 0 to 200° C. at 10° C. per minute scan rate to determine the Tg.

Coatings Formulations

Formulations for coatings evaluations were prepared using D.E.R.™ 331 (EEW 187.7 g/eq) and the hardener at a 1 to 1 epoxy to amine hydrogen (NH) equivalent ratio. Formulations (30 grams) were mixed using a Flack Tek mixer for 0.5 minute at 800 rpm followed by 2 minutes at 2400 rpm, then the mixture was transferred to a glass jar and centrifuged for 5 minutes at 2500 rpm. The time between mixing and applying the draw downs was 10-15 minutes, which included the centrifuge time. For each formulation, a 150 mil drawdown on a glass slide was made for dry film time (DFT) testing, and two draw downs with a 10 mil drawdown bar were made on phosphatized steel Q-panels (12 inch×4 inch) for gloss measurement, conical mandrel bend, and cross hatch adhesion. In addition, 13 grams of formulation was poured into a small aluminum pan for shore-D hardness development testing. All the coating draw downs were cured for 7 days at ambient (23° C.) prior to testing, except for the DFT test which was put on the DFT recorder right away.

Dry Film Time (DFT) Test

Dry times were determined by ASTM D 5895 using a BYK dry time recorder at the 48 hour speed setting. The test room temperature was 23° C. The end of the third stage was reported as the dust free time and the point at which the needle no longer penetrated the film was reported as the dry through time.

Coating Thickness

Coating thickness was measured using a Fischerscope Multi Measuring System instrument.

Gloss Measurement

Gloss was measured by ASTM D 523 at 20, 60, and 85 degree angles using a BYK Gardner micro-gloss 60° instrument, catalogue number 4510.

Conical Mandrel Bend

Coating flexibility and resistance to cracking was measured by ASTM D 522 using a Gardner unit with a ⅛ inch cone starting point.

Shore D Hardness

Hardness was measured by ASTM D2240 using a PTC Instruments Type D Durometer, model 307L. The shore-D hardness specimen was checked for hardness once sufficiently cured to a solid state and then at time intervals e.g. 24 hours, 48 hours, etc. until no further increase was observed.

Example 1

A polyamide based on BPEA, dimer fatty acid, and monomer fatty acid was synthesized according to the recipe shown in Table I below.

TABLE I

Example 1 Recipe

| | Eq wt g/eq | Equiv. | Actual g |
|---|---|---|---|
| UNIDYME 22 | 290.82 | 0.3167 | 92.90 |
| SYLFAT FA2 | 286.22 | 0.0524 | 14.99 |
| BPEA | 48.279 | 2.9846 | 146.3 |

The dimer fatty acid (UNIDYME 22) and monomer fatty acid (SYLFAT FA2) were charged to a 500-mL 5-neck glass reactor equipped with mechanical stirrer with stainless steel stir paddle, Dean stark trap with condenser, nitrogen inlet, addition funnel, heating mantel, and heating lamp. The mixture was warmed to 80° C. in a nitrogen atmosphere, with stirring, whereupon addition of BPEA was begun. The BPEA was added over 10 minutes, giving an exotherm up to 106° C. The mixture was heated to 100-110° C., then digested for 45 minutes, followed by heating up to 180° C. over a period of one hour, then holding 15 minutes. The mixture was then heated to 230-240° C. over a period of one hour then digested for a period of 30 minutes. Water formed during the reaction was distilled off and collected in the Dean stark trap. The total water collected was about 6 grams. The reaction gave a polyamide product which was an orange liquid with the following properties:

Amine Value: 596 mg KOH/g Viscosity (25° C.): 15280 cP

Gardner Color: 9

Unreacted BPEA in product: ~6.5 wt %.

Calculated Amine Hydrogen Equivalent Weight (AHEW): 172 g/eq NH

Comparative Example 1

A polyamide was synthesized by reaction of dimer acid, monomer acid, and TETA according to the recipe shown in Table II below.

TABLE II

Comparative Example 1 Recipe

|  | Eq wt g/eq | Equiv. | Target g | Actual g |
| --- | --- | --- | --- | --- |
| SYLFAT FA2 | 286.22 | 0.1817 | 52.00 | 52.17 |
| UNIDYME 22 | 290.82 | 1.0978 | 319.28 | 315.50 |
| TETA (D.E.H. 24) | 38.877 | 4.7726 | 185.55 | 183.9 |

The same operating procedure was used as Example 1, except after reaching 230° C. and digesting 15 minutes, vacuum operation was conducted for 30 minutes at 200 mmHg absolute pressure in order to drive off additional water and increase imidazoline content. The polyamide obtained was an orange liquid with the following properties (similar to Versamid 140):

Amine value 366 mg KOH/g

Viscosity (25° C.): 11800 cP

Gardner Color: 11

Unreacted TETA in product: ~2%

Imidazoline content (61 mole %)

Calculated AHEW: 117 g/eq NH

The polyamides from Example 1 and Comparative Example 1 were evaluated in formulations with D.E.R.™ 324 for mechanical properties and in formulations with D.E.R.™ 331 for coatings properties. A formulation with a 1:1 blend of the BPEA polyamide and the TETA polyamide was also evaluated. Note—D.E.R.™ 324 gives a lower Tg than D.E.R.™ 331 due to the presence of ~17% monoepoxy reactive diluent.

The results of the mechanical evaluations with D.E.R.™ 324 are shown in Table III. Comparing the BPEA polyamide to the TETA polyamide, the BPEA polyamide had:

Higher reactivity (gel time with DER™ 324 was 85 min vs. 380 min)

Higher % elongation at break (35% vs 12%)

The results of coating evaluations and a DSC reactivity study, both with D.E.R.™ 331, are shown in Table IV. The samples for coating evaluation were cured 7 days at ambient temperature (23° C.) prior to testing, unless noted otherwise. The DSC reactivity study showed an onset of exotherm at 39° C. with BPEA polyamide versus 53° C. with the TETA polyamide.

The dry time test also indicated faster reactivity with the BPEA polyamide, with a dust free time of 2.5 hr and complete dry through at 4 hr, versus 10 hour and >48 hour for the TETA polyamide. Shore D hardness development was faster in the sample cured with BPEA polyamide. The $1^{st}$ scan Tg of the shore D test samples after 7 days cure was similar for all three formulations, however, the $2^{nd}$ scan Tg was lower for the BPEA PA versus the TETA PA (74° C. vs. 90° C.).

The coatings adhesion and flexibility results were similar for the TETA polyamide and the BPEA polyamide, however, the appearance (gloss) was much better for the BPEA polyamide versus the TETA polyamide (60° gloss of 93 versus 65). The 1:1 blend formulation had gloss in between TETA polyamide and BPEA polyamide.

In summary, the BPEA polyamide gave the following characteristics versus the TETA polyamide:

Higher reactivity

Faster thin film set time

Faster Shore D hardness development

Better coating appearance

The BPEA polyamide solves the problem of slow reactivity of the TETA polyamide by having 4 times faster gel time of the curable resin and hardener, gives better quality film appearance, minimal or no induction time for the curable resin and hardener mixture, faster dry time, and gives better flexibility (higher percent elongation to break).

TABLE III

Mechanical Properties and Reactivity Results for D.E.R. 324 Cured with BPEA Polyamide vs. TETA Polyamide

|  | TETA PA (Comp Ex 1) | BPEA PA (Ex 1) | TETA-PA:BPEA-PA, 1:1 blend |
| --- | --- | --- | --- |
| Polyamide Viscosity, cP | 11807 | 15280 | 13420* |
| Polyamide Mix ratio with D.E.R. 324, phr | 58.5 | 86.0 | 69.6 |
| Gel Time (80 g mass), min | 380 | 85 | na |
| Plaque Cure Schedule | 60 C./15 hr | 60 C./15 hr | 60 C./15 hr |
| TENSILE |  |  |  |
| Tensile strength, MPa (std dev) | 43.1 (0.4) | 39.9 (0.6) | 42.2 (3.7) |
| Modulus, MPa | 2055 (133) | 2082 (178) | 2209 (236) |
| Elongation at Break, % | 12.4 (1.8) | 35.0 (8.7) | 15.3 (4.1) |
| 3-POINT FLEX |  |  |  |
| Ultimate Flex Strength, MPa | 67.6 (1.1) | 63.4 (1.0) | 70.4 (0.4) |
| Modulus, MPa | 1771 (26) | 1824 (54) | 2010 (17) |
| DMTA |  |  |  |
| Tg 1st scan | 74.1 | 56.7 | 64 |
| Tg 2nd scan | 74.2 | 59.5 | 66.9 |

Calculated viscosity of blend.

TABLE IV

Coatings and Reactivity Test Results for D.E.R.
331 Cured with BPEA Polyamide vs. TETA Polyamide

|  | TETA PA (Comp Ex 1) | BPEA PA (Ex 1) | 1:1 blend, (Comp Ex 1:Ex 1) |
|---|---|---|---|
| AHEW, g/eq NH | 117 | 172 | 139 |
| Part B Viscosity, cP | 11807 | 15280 | 13420 (calculated) |
| Mix ratio with Epoxy, phr | 62.3 | 91.6 | 74.2 |
| Calc'd Mix Viscosity, cP | 12029 | 13536 | 12680 |
| DSC Reactivity Study: | | | |
| DSC, onset exotherm, ° C. | 52.7 | 38.7 | 36.8 |
| DSC, peak exotherm, ° C. | 88.3 | 72.5 | 75.3 |
| Gel Time, 100 g mass | 163 | 40 | Not measured |
| Coatings Evaluations: | | | |
| Dry Time, Dust Free, hr | 10 | 2.5 | 3.7 |
| Dry Time, Dry Through, hr | >48 | 3.7 | >48 |
| Shore D hardness, 18 hr | 58 | 78 | 72 |
| Shore D hardness, 47 hr | 75 | 76 | 74 |
| Shore D hardness, 7 days | 77 | 77 | 77 |
| 1st scan Tg | 49 | 47 | 46 |
| 2nd scan Tg | 90 | 74 | 83 |
| Average Thickness, mil | 6.24 ± 0.55 | 6.53 ± 0.32 | 6.56 ± 0.2 |
| Cross hatch | 4B | 4B | 2B |
| Conical mandrel | Pass | Pass | Pass |
| 20° Gloss | 28.6 | 90.2 | 47.4 |
| 60° Gloss | 64.8 | 92.6 | 80.6 |
| 95° Gloss | 59.1 | 96.2 | 92.7 |

Example 2

A polyamide was synthesized by the same recipe and procedure as described in Example 1. The final product had an amine value of 612 mg KOH/g and a viscosity of 16351 cP.

Example 3

A polyamide was synthesized by reaction of BPEA (190.5 g), SYLFAT FA2 (24.3 g), and UNIDYME 22 (149.7 g) using the same procedure described in Example 1. The final product had an amine value of 551 mg KOH/g, and a viscosity of 28724 cP. The calculated AHEW was 200 g/eq NH.

The polyamides from examples 2 and 3 were evaluated for corrosion resistance versus Versamid 140, a commercially available polyamide. The test was conducted according to ASTM D1654. For this testing, D.E.R.™ 671-X75 was used as the epoxy resin (EEW=606.7 g/eq epoxy). A part A mixture was prepared with the weight percentage composition shown in Table V, below. The part A mixture was prepared using a Dispermat high shear mixer.

TABLE V

Part A Mixture for Corrosion Test Formulations

|  | Weight % |
|---|---|
| DER 671-X75 | 26.20 |
| TiO2 | 11.50 |
| D.E.R.* 331 | 1.65 |
| Talc | 30.70 |
| Xylene | 21.30 |
| Butanol | 8.65 |

The part A mixture was combined with the polyamides in the ratios set forth in Table VI, below followed by thorough mixing of each formulation.

TABLE VI

Formulations for Corrosion Testing

|  | Versamid 140 (comparative) | BPEA PA Ex 2 | BPEA PA Ex 3 |
|---|---|---|---|
| Part A, g | 28.54 | 27.26 | 27.01 |
| Polyamide, g | 1.50 | 2.47 | 2.86 |

Two panels of each formulation were prepared on cold blasted steel panels. The panels were cured for 7 days at ambient temperature, after which a scribe was placed on each panel. The panels were then placed in a salt fog chamber at 35° C. After 1000 hours, the panels were removed from the chamber and examined for corrosion and blistering. The results are shown in Table VII below.

TABLE VII

Corrosion Test Results (ASTM D714)

|  | Creep | Blister size rank | Blister Frequency | Rust |
|---|---|---|---|---|
| Versamid 140 - panel 1 | none | 4 | Few | none |
| Versamid 140 - panel 2 | none | 4 | Few | none |
| BPEA PA Ex 2 - panel 1 | none | 4 | Few | none |
| BPEA PA Ex 2 - panel 2 | none | 4 | Medium | none |
| BPEA PA Ex 3 - panel 1 | none | 4 | Medium | none |
| BPEA PA Ex 3 - panel 2 | none | 4 | Medium Dense | none |

The corrosion results show no significant difference in creep. The BPEA PA has slightly higher blistering than the commercial Versamid 140.

Example 4

A low viscosity polyamide, known in the art as an amidoamine, was synthesized by the reaction of BPEA (186.7 g), SYLFAT FA2 (144.4 g), and UNIDYME 22 (186.7 g) according to the procedure in Example 1. A light orange liquid product (336 g) was obtained with an amine value of 560 mg KOH/g, a viscosity of 917 cP and containing 6 wt % unreacted BPEA. The calculated AHEW was 201 g/eq NH.

The polyamide from Example 4 (95.1 g) was formulated with D.E.R. 324 (94.8 g) for mechanical property testing. The formulation was mixed on a Flack Tek mixer for 0.5 minutes at 800 rpm followed by 2 minutes at 1600 rpm. The mixture was centrifuged for 5 minutes at 2500 rpm, and was then poured into a mold which had been pre-warmed to 40° C. The mold was placed in an oven for 15 hours at 60° C. The resulting plaque was used to prepare specimens for tensile testing (ASTM D1708) and Tg determination (by DSC, 2 scans from −50° C. to 200° C.). The results are summarized below:

1$^{st}$ scan Tg: 23° C.

2$^{nd}$ scan Tg: 26° C.

Percent elongation: 158% (±7.0)

The polyamide from example 4 (51.7 g) was formulated with D.E.R. 331 (48.3 g) for gel time and dry film time measurements. For comparison, a sample of commercially available Versamid 140 (35.4 g) was formulated with D.E.R. 331 (35.4 g). An additional comparative formulation was made with D.E.R. 331 (66.8 g) and Genamid 747 (33.1 g). The results are summarized in Table VIII below.

TABLE VIII

Gel Time and Dry Time Measurements

|  | BPEA Polyamide Ex 4 | Genamid 747 (comparative) | Versamid 140 (comparative) |
|---|---|---|---|
| Gel time, minutes (100 g mass) | 67 | 182 | 163 |
| Dry time, dust free, hr | 5 | 11 | 8 |
| Dry time, dry through, hr | 12 | >48 | >48 |

In summary, the BPEA polyamides have higher reactivity with epoxy resins than standard polyamides, for instance:

Shorter gel time

Faster dry time (coatings)

Lower onset temperature of exotherm by DSC

The coatings from the BPEA polyamides and epoxy resins have better film appearance than standard polyamide cured epoxy resins, as evidenced by the higher gloss in a clear coat formulation. In addition, the formulations do not require an induction time prior to application.

The invention claimed is:

1. A polyamide composition comprising a reaction product of:
    a) an excess of a polyfunctional amine having the formula:

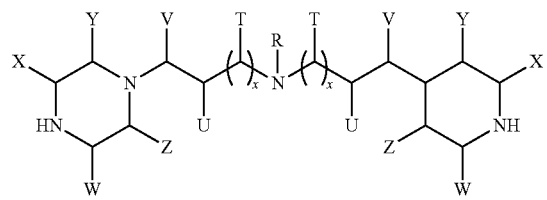

wherein each R, T, U, V, W, X, Y, and Z group is the same or different and is selected from hydrogen, or a hydrocarbyl group; and the value of x is 0 to 10, with the proviso that if x is greater than 1, each T may be the same or different; with at least one of
    b) a dimer fatty acid; and
    c) a monomer fatty acid having the formula RCOOH wherein R is a saturated or unsaturated aliphatic carbon chain of 10 to 21 carbon atoms wherein the amount of the polyfunctional amine ranges from 30 to 80 wt. %, based on the total weight of reactants used to make the polyamide.

2. A polyamide composition in accordance with claim 1 wherein said polyfunctional amine is bis(2-(piperazin-1-yl)ethyl)amine.

3. A polyamide composition in accordance with claim 1 wherein said dimer fatty acid is present in an amount in the range of from 70 weight percent to 95 weight percent, based on the total weight of said monomer fatty acid and said dimer fatty acid.

4. A polyamide composition in accordance with claim 1 which is a reaction product of a) said excess of a polyfunctional amine, with at least one of b) and c) wherein b) is said dimer fatty acid, and c) is said monomer fatty acid, and additionally d) a polycarboxylic acid other than a dimer fatty acid.

5. An oligomeric composition comprising a polyamide composition in accordance with claim 1 having the formula

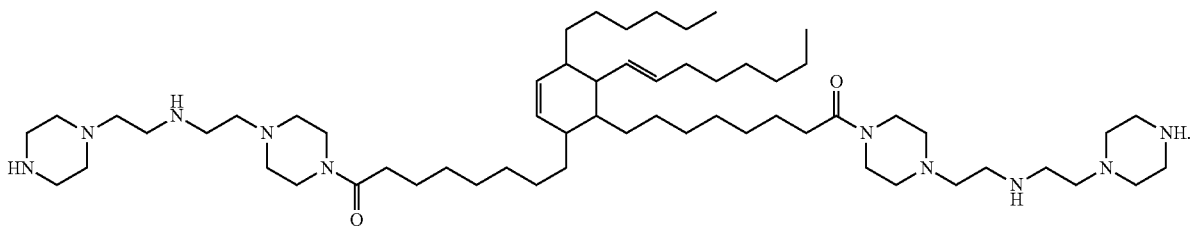 [SMILES: CCCCCC/C=C/C1C(CCCCCC)C=CC(CCCCCCCC(=O)N2CCN(CCNCCN3CCNCC3)CC2)C1CCCCCCCC(=O)N1CCN(CCNCCN2CCNCC2)CC1]

6. An oligomeric composition comprising a polyamide composition in accordance with claim 1 having the formula

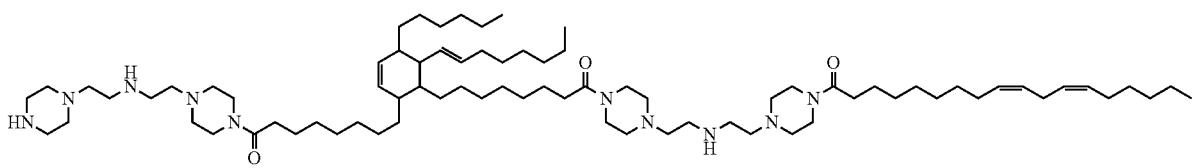 [SMILES: CCCCC/C=C\C/C=C\CCCCCCCC(=O)N1CCN(CCNCCN2CCN(C(=O)CCCCCCCC3C(CCCCCCCC(=O)N4CCN(CCNCCN5CCNCC5)CC4)C=CC(CCCCCC)C3/C=C/CCCCCC)CC2)CC1]

7. An oligomeric composition comprising a polyamide composition in accordance with claim 1 having the formula

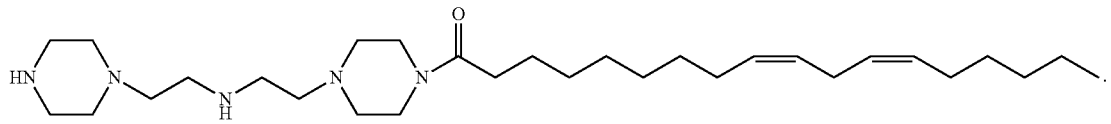 [SMILES: CCCCC/C=C\C/C=C\CCCCCCCC(=O)N1CCN(CCNCCN2CCNCC2)CC1]

8. A polyamide composition in accordance with claim 1 wherein a second amine comprising a polyalkylene-amine is present in combination with said polyfunctional amine.

9. A method for preparing the polyamide composition of claim 1 comprising: contacting a) said polyfunctional amine; with at least one of b) said dimer fatty acid; and c) said monomer fatty acid in a reaction zone under reaction conditions.

10. A method in accordance with claim 9 wherein the components are contacted in said reaction zone in a ratio of combined primary plus secondary amine to carboxylic acid equivalents in the range of from 1 to 12.

11. A method in accordance with claim 9 wherein said polyfunctional amine comprises bis(2-(piperazin-1-yl)ethyl) amine and is present in the reaction zone in the range of from 30 weight percent to 80 weight percent, based on the total weight of reactants charged.

12. A curable composition comprising:
a) an epoxy resin; and
b) a hardener comprising the polyamide composition of claim 1.

13. A curable composition in accordance with claim 12, further comprising a hardener other than said polyamide composition.

14. A curable composition in accordance with claim 12 wherein the epoxy resin is selected from the group consisting of bisphenol A diglycidyl ether, bisphenol F diglycidyl ether, and mixtures thereof.

15. A curable composition in accordance with claim 12 having an epoxide to amine hydrogen equivalent ratio in the range of from 0.7 to 1.3.

16. A process for preparing a thermoset comprising curing the curable composition of claim 12.

17. An article prepared from the curable composition of claim 12.

18. An article in accordance with claim 17, wherein the article is selected from the group consisting of a coating, a composite, an adhesive, and an electrical laminate.

\* \* \* \* \*